United States Patent [19]

Swann

[11] Patent Number: 4,504,582

[45] Date of Patent: Mar. 12, 1985

[54] VERMICULITE AS A CARRIER SUPPORT FOR IMMOBILIZED BIOLOGICAL MATERIALS

[75] Inventor: Wayne E. Swann, Columbia, Md.

[73] Assignee: Genex Corporation, Rockville, Md.

[21] Appl. No.: 464,376

[22] Filed: Feb. 7, 1983

Related U.S. Application Data

[63] Continuation-in-part of Ser. No. 400,141, Jul. 20, 1982, abandoned.

[51] Int. Cl.$^3$ .................. C12P 13/22; C12P 13/20; C12N 11/14; A61K 9/28
[52] U.S. Cl. .................... 435/108; 424/23; 424/78; 424/85; 424/88; 435/109; 435/176; 435/177; 435/178; 435/180; 435/181; 435/182
[58] Field of Search .................. 424/23, 78; 435/108, 435/109, 176, 177

[56] References Cited

U.S. PATENT DOCUMENTS

| | | | |
|---|---|---|---|
| 3,274,052 | 9/1966 | Yaffe et al. | 424/23 |
| 3,453,360 | 7/1969 | Hill et al. | 424/23 |
| 3,791,192 | 2/1974 | Chitaba et al. | 435/182 X |
| 3,830,699 | 8/1974 | Zaborsky | 435/180 |
| 3,859,169 | 1/1975 | O'Driscoll | 435/182 |
| 4,248,969 | 2/1981 | Lee | 435/176 |
| 4,266,029 | 5/1981 | Branner-Jorgensen | 435/176 |
| 4,323,650 | 4/1982 | Rosevear | 435/176 |

FOREIGN PATENT DOCUMENTS 2019410 10/1979 United Kingdom .

OTHER PUBLICATIONS

Pinck, et al., *Soil Sci.*, 94: 129 (1962).
Wykes, et al., Biochim Acta 286:260-268 (1972).
Horvath, C., Biochim. Biophys. Acta 358:164-177 (1974).
Sundaram, et al., Clinical Chemistry 24(10); 1813-1817 (1978).
Marshall, et al., Carbohydrate Research 25:489-495 (1972).
Chibata, I., Immobilized Enzymes Research and Development, John Wiley & Sons, N.Y. (1978) p. 31-33.

*Primary Examiner*—Sam Rosen
*Attorney, Agent, or Firm*—Bernard, Rothwell & Brown

[57] ABSTRACT

Biological materials are immobilized by being absorbed into vermiculite particles which then are coated with a polymeric coating material. A variety of cross-linking, condensing, and gelling agents may be used to strengthen and crosslink the polymer.

36 Claims, No Drawings

# VERMICULITE AS A CARRIER SUPPORT FOR IMMOBILIZED BIOLOGICAL MATERIALS

This is a continuation-in-part of application Ser. No. 400,141, filed July 20, 1982, now abandoned.

TECHNICAL FIELD

This invention relates to a method for immobilizing biological materials. More particularly, the invention relates to the immobilization of biological materials wherein the materials are absorbed by vermiculite particles which then are coated with a polymer.

BACKGROUND

Biological materials such as enzymes or enzyme-producing microorganisms or cells, are often used as catalysts for synthetic reactions and for analytical techniques. Such catalysts are desirable because they operate with high specificity and efficiency under generally mild reaction conditions.

Because enzymes and other biocatalysts are generally water-soluble, they are suited for use in batch-type reaction systems. Reuse of such enzymes and other biocatalysts is limited because of difficulties in recovering those materials from the spent reaction medium in active or usable form. Moreover, the materials tend to remain in the prepared product as contaminants. In order to avoid these problems, methods have been developed to immobilize biological materials which exhibit catalytic activity on insoluble solid supports. Immobilization is intended to result in a stabilized biological material which can withstand the rigors of repeated or continuous use.

Several immobilization systems for biological materials have been reported. Enzymes have been immobilized by absorption onto insoluble materials such as charcoal, glass, cellulose, calcium phosphate gel, montmorillonite and organic ion-exchange resins among others. Immobilization has also been achieved by entrapment within starch and acrylamide gels, covalent attachment between enzymes and insoluble organic polymers, as well as covalent attachment between enzyme molecules themselves.

The processes of the prior art often result in products of reduced biological activity, when compared with those of the corresponding unbound biological material. These biological materials are known to be sensitive to thermal and chemical denaturation or inactivation. The loss of biological activity often results when immobilizing operations are carried out under harsh conditions which can be particularly problematic when polymer condensation reactions are involved. Furthermore, the products resulting from prior art methods are often disadvantageous with respect to their hydrophilicity, strength, durability, and porosity.

It therefore is an object of the present invention to develop a method of immobilizing biological materials that does not reduce the biological activity of the products.

It is a further object of this invention to develop a method of immobilizing biological materials wherein the resulting products exhibit excellent strength, durability, porosity, and biological stability. Yet another object of the invention is to provide a method of immobilizing a high quantity of biological material per unit volume of final support (high density).

DISCLOSURE OF THE INVENTION

It now has been discovered that biological materials can be immobilized in a simple and very economical manner while maintaining a high degree of their catalytic activity. The method of the present invention produces an insolubilized biological material composite which contains biological material entrapped within vermiculite particles coated with a polymer. Depending upon the polymer chosen and the nature of the biological material entrapped within the vermiculite, it may be advantageous to crosslink or condense the polymer. Very little loss of activity occurs when the composite is prepared, and such composites exhibit excellent strength and durability. Furthermore, when the polymer is cross-linked or condensed, the hydrophilicity of these materials can be adjusted by varying the extent of crosslinking or condensation. The method of the present invention produces a composite which can be separated from reaction mixtures by simple filtration, or used in continuous reaction processes such as those wherein a reacting substrate flows through a packed column reactor.

In accordance with the method of the present invention, vermiculite particles are contacted with the biological material, such as whole wet cells harvested from a fermentation broth. The biological material is absorbed into the vermiculite particles. A polymeric coating material is added to the vermiculite so as to coat the particles. Various crosslinking, condensing and gelling agents then can be added to crosslink and strengthen the polymer and/or the biological material to form a hard permeable coating. The polymer optionally may be combined with a polycarboxylic acid to form a water soluble pre-polymer before being mixed with the vermiculite. This procedure results in the formation of a biological material composite wherein the biological material is immobilized within the polymer coated vermiculite.

Immobilization of biological material within the vermiculite can occur by physical entrapment, by covalent bonding of the polymer via the crosslinking or condensing agent and reactive groups on the biological material, or by crosslinking within the vermiculite particles via a suitable crosslinking material. For example, when the polymer is a polyalkyleneimine, the biological material can be immobilized through covalent linkage, since amine and carboxylic groups of the biological material can substitute for either an amine group on the polyalkyleneimine or a carboxylic group on a polycarboxylic acid which can be added to the coated vermiculite. Covalent linkage to the polymer ultimately occurs through a condensing agent.

The method of the present invention allows the preparation of a wide variety of biological material composites. The biological material can include enzymes, microbial cells, antigens, antibodies, antibiotics, coenzymes, plant cells, animal cells, bacteria, yeasts, fungi, tissue cultures or mixtures thereof. Biological materials are preferably added to the vermiculite in aqueous form.

It has been discovered that vermiculite makes an excellent carrier for the immobilization of biological material. Vermiculite particles are capable of absorbing very large quantities of biological materials, thus resulting in high density loading. Vermiculite also is very inexpensive and readily available, making it highly beneficial for use as a carrier in large scale production of products. Finally, the resulting immobilization support resulting from this method of immobilizing biological material is rigid and highly active.

It has been determined that the particle size of the vermiculite used in the immobilization process of this invention can vary substantially. For example, the particle size of the vermiculite can vary from a fine powder to about 1 cm., preferably about 0.5 to 1 mm. The amount of biological material added to the vermiculite can vary according to the specific end use of the biological material composite. Generally it ranges from about 0.001 to 2 g (dry weight basis) per gram of vermiculite used, preferably from about 0.01 to about 1 g per gram of vermiculite.

The biological material composites prepared by the method of this invention can differ greatly in hydrophilicity, strength, durability, and porosity. Decreasing the extent to which the polymer used to coat the vermiculite is crosslinked or condensed can result in a composite having greater hydrophilicity. The addition of multifunctional cross-linking agents can increase the strength and durability of the polymer-vermiculite-biological material composite, where the additional functional groups further condense the polymer and cause a more hydrophobic composite.

The overall porosity of the matrix can be increased by the addition of a water-soluble particulate material to the polymer mixture before it is completely condensed. The dry material is removed subsequently by the addition of water after condensation, which dissolves the solid. The portion of the composite formerly displaced by the solids are left empty, thus increasing the porosity of the matrix. Any water-soluble particulate material that does not adversely affect the polymer, vermiculite or biological material significantly may be employed for increasing the porosity of the mixture. Water soluble polycarboxylic acids, such as those reacted with the uncondensed polymers, are particularly suited to increasing matrix porosity, since excess amounts utilized to increase porosity do not substantially interfere with the condensation reactions.

The polymers used in the method and composites of the present invention generally vary in molecular weight, depending on reaction conditions, and preferably have a branched chain structure. A variety of polymeric materials can be used in the method of this invention, including polyalkyleneimines, polysaccharides, polyacrylamide, polyurethane, alginate, and cargeenan. Preferred polymers are polyalkyleneimines.

Polyalkyleneimines can be synthesized by the acid-catalyzed addition polymerization of alkylene imine monomers. A preferred polyalkyleneimine is polyethyleneimine (PEI) because it is currently readily available at relatively low cost, and it functions well in the condensation reactions employed in the present method. Polyethyleneimine is produced by ring-opening polymerization of ethyleneimine in the presence of catalysts, such as mineral acids. The polymer is highly branched and contains primary, secondary and tertiary amino groups. PEI is water-soluble, and upon crosslinking or condensation of the polymer chains, a water-insoluble product results.

The polyethyleneime can be crosslinked with an amine cross-linking agent to impart additional stability and strength. This treatment results in entrapped biological material, with some crosslinking between the polyalkyleneimine and free amine groups of the biological material. Cross-linking agents include glutaric dialdehyde, diisocyanates, polyisocyanates, 2,4,6-trichloro-s-triazine, bisoxirane, bisimidate, divinylsulfone, 1,5-difluoro-2,4-dinitrobenzene, and the like. Glutaric dialdehyde is preferred for this purpose.

The polymer chosen generally is added to the composite in an amount sufficient to substantially coat the vermiculite particles, and this amount will vary substantially, depending on the particle size of the vermiculite, the nature of the biological materials and the physical properties desired. Generally, the polymer can range from about 0.5 to about 25% by wt. of the composite, and preferably ranges from about 2% to about 15% by wt. of the composite. The amount of crosslinking and/or condensing agent employed is related to the amount of polymer, as hereinafter discussed.

When the polymer is polyethyleneimine, a highly efficient method of condensation utilizes a polycarboxylic acid (PCA) to bridge amine groups on adjacent PEI chains. Condensing agents, preferably carbodiimides, readily effect the condensation. The reactions involved in making the condensed polyethyleneimine of the present invention are illustrated below:

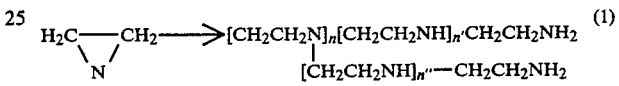

(1)

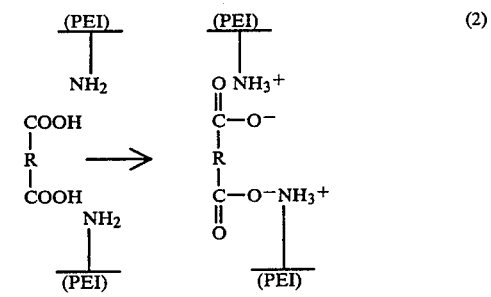

(2)

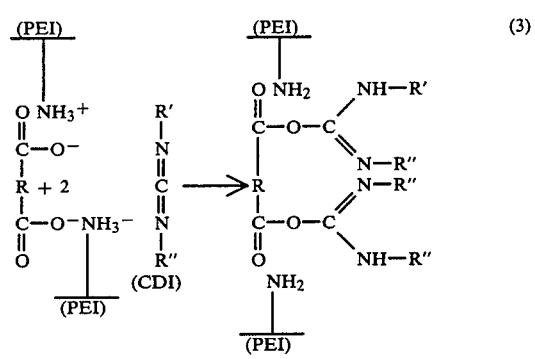

(3)

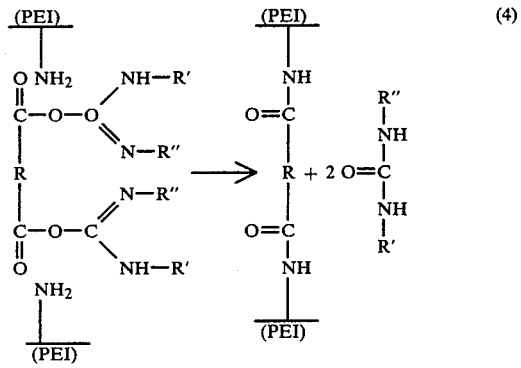

(4)

Reaction (1) illustrates the polymerization of ethyleneimine to form PEI having a branched-chain structure, wherein n and n' are integers greater than 0 and n" may be 0 (indicating that the [CH$_2$CH$_2$NH] group is absent) or greater than 0. Reaction (2) shows the formation of a salt of the amine groups of PEI with a polycarboxylic acid, wherein R can be a substituted or hydrocarbon groups, reactions (3) and (4) show the condensation of the PEI and polycarboxylic acid, using a carbodiimide condensing agent. R and R' are hydrocarbon groups, which, along with other reactants and conditions of the illustrated reactions, are described more fully below.

In general, polycarboxylic acids suited for use in the present invention may be substituted or unsubstituted carboxylic acids having at least two carboxylic groups. Preferably, the polycarboxylic acids are water-soluble, so that they may be utilized to increase the porosity of the composite, as well as for condensing the polyalkyleneimine. Examples of polycarboxylic acids that can be employed in the methods and composites of the present invention include adipic, azelaic, 1,11-undecanedioic, 1,12-dodecanedioic, traumtic, pentadecanedioic, hexadecanedioic, sebacic, suberic, glutaric, malonic, pimellic, succinic, malic, maleic, glutamic, aspartic, oxalic, fumaric, polyaspartic, and the like. Dicarboxylic acids are preferred for use in the present invention and include maleic acid, succinic acid, glutaric and adipic acid. Higher polycarboxylic acids can be any substance that contains two or more carboxylic acid groups, and include high molecular weight polymeric materials, such as polyaspartic acid, having a molecular weight of from 5,000 to 50,000. The condensation reactions are generally exothermic, therefore, the reaction mixtures are advantageously cooled to a temperature that is not deleterious to the biological material being immobilized, e.g., about 37° or lower.

The molar ratio of polycarboxylic acid to polyalkyleneimine (PCA:PAI) can vary widely, because of the variation in molecular weight of the reactants. Generally, such ratio ranges from 1:20 to 1:0.0005. Where polycarboxylic acid is added to increase the porosity of the composite of the present invention, a considerable molar excess of polycarboxylic acid is often employed.

The polycarboxylic acid can be added in a condensing amount to the polyalkyleneimine under prepolymerizing conditions to form a water-soluble prepolymer. The prepolymer is generally a viscous liquid, to which the vermiculite containing the immobilized biological material conveniently can be added and maintained in suspension during the condensation reaction. The condensing agent is then added to effect condensation and solidification of the prepolymer-vermiculite composite. The pH of the reaction mixture is maintained at a level which does not substantially inactivate or adversely affect the biological material. The pH can range from about 2 to about 12 and preferably ranges from about 5 to about 10.

As noted above, to effect condensation of polyalkyleneimine chains through polycarboxylic acids, a condensing agent is advantageously employed. Generally, any condensing agent that catalyzes or facilitates the reaction of amines and carboxylic acids can be used. Examples of such condensing agents include N-ethyl-5-phenyl—isoazolium-3- sulfonate, n-ethoxycarbonyl-2-ethoxy-1,2-1,2-dihydroquinoline, and various carbodiimides. Carbodiimide condensing agents that can be used in the composition of the present invention have the formula R'—N=C=N—R" where R' and R" are hydrocarbyl groups containing from 3 to about 20 carbon atoms, preferably from about 5 to about 12 carbon atoms. Such condensing agents include 1-ethyl-3,3-dimethylaminopropyl carbodiimide, dicyclohexyl carbodiimide, 1-cyclohexyl-3- (2-morpholinoethyl) carbodiimidemetho-p-toluene sulphonate, or salts thereof. Carbodiimide condensing agents are added to the reaction mixture in a condensing amount, which generally is substantially a stoichiometric amount; e.g. from about 0.2 to 3 times, preferably from about 0.5 to 1.5, a stoichiometric amount. Each carbodiimide molecule reacts with a single acid group of the polycarboxylic acid. For example, carbodiimide to dicarboxylic acid molar ratios of about 2:1 are generally used in the method of the present invention. Upon addition of the condensing agent at room temperature, noticeable polymerization results within thirty seconds, and is generally complete within about two hours.

When the polyethyleneimine has been insolubilized by the addition of a condensing agent, an optional post treatment step involves cross-linking the condensed, coated vermiculite with an amine cross-linking agent, such as glutaric dialdehyde, as described above, to provide additional strength and stability to the final composite.

Depending upon the type of polymer chosen a variety of condensing and cross-linking agents may be selected from those known in the art to strengthen the composite. By the use of the described methods of the present invention it is possible to immobilize a wide variety of biological materials to produce novel biocatalytic composites.

In the following examples, the immobilization procedures are described in greater detail. These examples describe the manner and process of making and using the invention and set forth various embodiments of the invention, but are not to be construed as limiting.

EXAMPLE I 80 grams of aspartase-containing E.coli cell paste, containing about 75% water by weight, was prepared from fresh aspartase-containing E.coli. To make the paste, the fermentation medium was prepared by dissolving in one liter of water, 24 grams of yeast extract, 30 grams of fumaric acid, 2 grams of sodium carbonate, 2 mM magnesium sulfate, and 0.1 mM calcium chloride, and the pH was adjusted to about 7.2 with ammonium hydroxide. This medium was inoculated with 1 ml. of a culture of E.coli (ATCC No. 31976) that had been incubated for 12–16 hours at 37° C. in a peptone medium containing 0.5 percent monosodium glutamate. The inoculated medium was incubated for 12–14 hours at 37° C. The cells were harvested by centrifuging at 5000 rpm for 30 minutes.

The 80 grams of aspartase containing E.coli were added to 20 grams of vermiculite particles. After the cell paste was allowed to absorb into the vermiculite, 10 grams of polyethyleneimine were added to the mixture and stirred until evenly distributed. Glutaric dialdehyde (20 grams of a 25% solution in water) was then added and mixed until hard particles resulted. A second batch of material was made by the same procedure. Both batches of material were left to dry overnight.

The material was packed into a column with a final bed volume of 353 cc. The column then was used to convert ammonium fumarate to L-aspartic acid. A 1.5 M solution of ammonium fumarate with 1 mM magnesium sulfate, pH 8.5, at 37° C. was passed through the column at 360 cc/hr (1.0 SV$^{h-1}$). The effluent was monitored for aspartase activity by measuring the disappearance of fumaric acid on a spectrophotometer at 240 nm. The column was in continuous operation for 151 days. During that time samples of the column effluent were assayed to determine the % conversion of the substrate. The results are shown in Table 1.

TABLE 1

| Day | % conversion of 1.5 M ammonium fumarate (1 pass at 1 SV/h) |
|---|---|
| 1 | 98.2 |
| 6 | 99.2 |
| 16 | 99.4 |
| 26 | 99.2 |
| 37 | 99.0 |
| 55 | 98.7 |
| 90 | 98.2 |
| 120 | 91.0 |
| 151 | 91.3 |

EXAMPLE II

The general procedure of Example I was followed using 120 grams of cell paste and 15 grams of polyethyleneimine. One batch of immobilized material was packed into 173 cc bed volume column reactor. The column was successful in converting 99% of a 1.8 M ammonium fumarate solution at 360 cc/hr (2.08 SV$^{h-1}$). The productivity of this column is calculated at 493 gms L-aspartic acid produced/liter bed volume immobilized cells/hour at 37° C. (3.7 mol/1/hr).

EXAMPLE III

Ten batches of immobilized E.coli cells (100 grams of vermiculite/batch) were made by the general procedure of Example II.

The biocatalyst was then packed into a 12.5 liter bed volume column. Ammonium fumarate (1.8 M) at 37° C. was passed through the column at various flow rates, and the effluent was assayed for conversion of ammonium fumarate as in Example I. Table II shows the results of the test.

TABLE II

| Flow Rate (l/hr) | % Conversion (Fumaric Acid) | Kg/hr. (L-Aspartic Acid) | mol/l/hr. (L-Aspartic Acid) |
|---|---|---|---|
| 12.50 | 99.1 | 2.97 | 1.79 |
| 18.75 | 97.5 | 4.38 | 2.63 |
| 25.00 | 95.0 | 5.69 | 3.42 |
| 62.50 | 56.00 | 8.38 | 5.04 |

EXAMPLE IV

The general procedure of Example III was repeated with a frest batch of E.coli cells with the exception that the fresh cells contained 29% more activity than had the previous batch. When the substrate was passed through the column at 62.5 l/hr (as in Example III) the amount of aspartic acid produced was 10.56 kg/hr (6.35 mol/1/hr). This is a 27% increase in productivity over Example III.

EXAMPLE V

The enzyme tryptophan synthetase can be used in the process of this invention to catalyze the conversion of indole and serine to tryptophan. Vermiculite particles (2 grams) and 4 ml of crude tryptophan synthetase extract solution from E.coli cells were mixed together. The extract was allowed to absorb into the vermiculite. Polyethyleneimine (1 gram) was then added to the mixture to coat the vermiculite particles. Glutaric dialdehyde (2 ml of a 25% solution in water) was then added and mixed until hard coated particles resulted. The entire amount of material was then placed into a column and washed with a substrate solution consisting of 0.05 M serine, 0.05 M indole, 0.005 M glutathione, 0.005 M potassium phosphate dibasic and 200 mg. pyridoxal-5-phosphate/liter, pH adjusted to 7.8. The column then was used repeatedly in a batch recirculating system to produce 80 mg of L-tryptophan in 24 hours.

EXAMPLE VI

Nine grams of whole yeast cells R. rubra containing the enzyme phenylalanine ammonia-lyase were mixed into 3 grams of vermiculite particles, allowed to absorb into and thoroughly coat the particles, then cooled to 10° C. A polysaccharide coating solution was made by adding 0.8 grams of Kelco polysaccharide (K9A50) powder into 100 ml of deionized water at 80° C. and stirring for 10 minutes. The powder dissolved and 1 gram of potassium chloride was added to the solution. The solution was allowed to cool to 50° C. (remaining a solution). The warm solution was then poured over the cold vermiculite material while mixing. The polysaccharide formed a gel very rapidly, coating the vermiculite particles that contained R. rubra. The particles were placed in 100 ml of 0.1 M Potassium Phosphate buffer, pH 7.0 and thoroughly stir-washed. the particles were removed from the buffer solution. the solution showed no signs of cloudiness or haziness and was virtually free of yeast cells, indicating immobilization was successful. The particles were placed in 50 ml of 0.1 M ammonium cinnamate at pH 9.3 and the solution was tested for PAL activity through monitoring the production of L-phenylalanine. The immobilized cell material was successful in the production of L-phenylalanine; increasing amounts of L-phenylalanine were observed in the reaction solution over time.

What is claimed is:

1. A method for immobilizing biological materials by preparing an insolubilized biological material composite comprising the steps of:
   (a) adding vermiculite particles to an aqueous medium of biological material;
   (b) allowing said aqueous medium of biological material to absorb into said vermiculite; and
   (c) coating said vermiculite with a polymer.

2. A method according to claim 1 wherein the coated vermiculite of step (c) is crosslinked with a cross-linking agent or condensed with a condensing agent.

3. A method according to claim 1 or 2 wherein the polymer is selected form the group consisting of polyalkyleneimines, polysaccharides, polyacrylamide, polyurethane, alginate, and carageenan.

4. A method for immobilizing biological materials by preparing an insolubilized biological material composite comprising the steps of:
   (a) adding vermiculite particles to an aqueous medium of biological material;
   (b) allowing said aqueous medium of biological material to absorb into said vermiculite;
   (c) coating said vermiculite with a polyalkyleneimine polymer; and (d) crosslinking said coated vermiculite with an amine cross-linking agent or condensing with a condensing agent.

5. A method according to claim 4 wherein said polymer coated vermiculite is mixed with a cross-linking amount of an amine cross-linking agent to immobilize biological material within said coated vermiculite.

6. A method according to claim 4 wherein said polyalkyleneimine polymer is mixed with a condensing amount of a polycarboxylic acid to produce a partially polymerized precondensed water soluble polymer before it is mixed with said vermiculite.

7. A method according to claim 4 wherein said coated vermiculite is condensed by adding a condensing amount of a carbodiimide condensing agent under condensing conditions.

8. A method according to claim 6 wherein said coated vermiculite is condensed by adding a condensing amount of a carbodiimide condensing agent under condensing conditions.

9. A method according to claims 7 or 8, further comprising modifying the insolubilized biological material composite by post-treatment with an amine cross-linking agent to impart additional strength and stability to the composite.

10. The method of claim 4, 5, 6, 7 or 8, wherein the polyalkyleneimine polymer is selected from the group consisting of polyethyleneimine, polypropyleneimine, polybutyleneimine and polypentyleneimine.

11. The method of claim 4, 5, 6, 7 or 8 wherein the polyalkyleneimine polymer is polyethyleneimine.

12. The method of claim 6 or 8 wherein the polycarboxylic acid is selected from the group consisting of maleic acid, succinic acid and adipic acid.

13. The method of claim 7 or 8 wherein the carbodiimide condensing agent is selected from the group consisting of 1-ethyl-3,3-dimethylaminopropyl carbodiimide hydrochloride, dicyclohexyl carbodiimide, and 1-cyclohexyl 3-(2-morpholinoethyl) carbodiimidemetho-p-toluene sulphonate and salts thereof.

14. A method according to claims 4 or 5 wherein said amine cross-linking agent is selected from the group consisting of glutaric dialdehyde, diisocyanates, polyisocyanates, 2,4,6-trichloro-5-triazine, bisoxirane, bisimidate, divinyl-sulfone, and 1,5-difluoro-2,4-dinitrobenzene.

15. A method according to claim 1 or 4 wherein the amount of said biological material added to said vermiculite is about 0.001 to about 2 g. on a dry weight basis per gram of vermiculite.

16. The method of claim 6 wherein the molar ratio of polycarboxylic acid to polyalkyleneimine is from about 1:20 to 1:0.0005.

17. The method of claim 16, wherein the carbodiimide is employed in an amount ranging from about 0.2 to 3 times stoichiometric, relative to the polycarboxylic acid.

18. The method of claim 16, wherein the carbodiimide is employed in an amount ranging from about 0.5 to 1.5 times stoichiometric relative to the polycarboxylic acid.

19. The method of claim 1 or 4 wherein the biological material immobilized is selected from the group consisting of enzymes, microbial cells, antigens, antibodies, antibiotics, co-enzymes, bacteria, yeast, fungi, plant cells, animal cells, and tissue cultures.

20. The method of claim 1 or 4 wherein the biological material is microbially produced aspartase.

21. A method according to claim 1 or 4 wherein the enzyme is tryptophan synthetase.

22. An insolubilized biological material composite comprising a biologically active material adsorbed into particles of vermiculite which are immobilized within a polymer.

23. An insolubilized biological material composite comprising a biologically active material adsorbed into particles of vermiculite which are immobilized within a polymer, wherein said polymer is cross-linked with a cross-linking agent.

24. The insolubilized biological material composite of claim 23 wherein the polymer is a polyalkyleneimine and the cross-linking agent is an amine cross-linking agent.

25. The composite of claim 24 wherein the amine cross-linking agent is selected from the group consisting of glutaric dialdehyde, diisocyanates, polyisocyanates, 2,4,6-trichloro-S-triazine, bisoxirane, bisimidate, divinyl sulfone, and 1,5-difluoro-2,4-dinitrobenzene.

26. The composite of claim 24 wherein the amine cross-linking agent is glutaric dialdehyde.

27. An insolubilized biological material composite comprising a biologically active material adsorbed into particles of vermiculite which are immobilized within a polymer wherein said polymer is condensed with a condensing agent.

28. The insolubilized biological material composite of claim 27 wherein the polymer is a polyalkyleneimine and the condensing agent is a carbodiimide condensing agent.

29. The composite of claim 28 wherein the condensing agent is selected from the group consisting of 1-ethyl-3,3-dimethylaminopropylcarbodiimide hydrochloride, dicyclohexyl carbodiimide, and 1-cyclohexyl-3(2-morpholinoethyl)carbodiimide-metho-p-toluene sulphonate and salts thereof.

30. The composite of claim 24 or 26 wherein the polyalkyleneimine polymer is selected from the group consisting of polyethyleneimine, polypropyleneimine, polybutyleneimine, and polypentyleneimine.

31. The composite of claim 22, 23, 24, 27 or 28 wherein the biologically active material is selected from the group consisting of enzymes, microbial cells, antigens, antibodies, antibiotics, coenzymes, plant cells, animal cells, bacteria, yeast, fungi and tissue cultures.

32. the composite of claim 22, 23, 24, 27 or 28 wherein the biologically active material is aspartase.

33. The composite of claim 22, 23, 24, 27 or 28 wherein the biologically active material is tryptophan synthetase.

34. A method for producing aspartic acid comprising contacting, under aspartic acid producing conditions, a substrate containing ammonium fumarate with an insolubilized biological material composite of aspartase or aspartase containing microbial cells absorbed into vermiculite particles and immobilized within a polymer, wherein the immobilized vermiculite is cross-linked with a cross-linking agent or condensed with a condensing agent.

35. A method for producing tryptophan comprising contacting, under tryptophan producing conditions, a substrate containing indole and serine with an insolubilized biological material composite of tryptophan synthetase or tryptophan synthetase containing microbial cells absorbed into vermiculite particles and immobilized within a polymer, wherein the immobilized vermiculite is cross-linked with a cross-linking agent or condensed with a condensing agent.

36. A method for producing L-phenylalanine comprising contacting, under L-phenylalanine producing conditions, a substrate containing ammonium cinnamate with an insolubilized biological material composite of phenylalanine ammonia lyase or phenylalanine ammonia lyase-containing microbial cells absorbed into vermiculite particles and immobilized within a polymer.

* * * * *